(12) United States Patent
Karakoca

(10) Patent No.: US 11,833,318 B2
(45) Date of Patent: Dec. 5, 2023

(54) RESECTOR BALLOON WITH SHOCK ABSORBER PADDING AND RIGID OR FLEXIBLE CATHETER

(71) Applicant: YKK SAĞLIK HİZMETLERİ ANONİM ŞİRKETİ, Şişli-İstanbul (TR)

(72) Inventor: Yalçin Karakoca, Tuzla-Istanbul (TR)

( * ) Notice: Subject to any disclaimer, the term of this patent is extended or adjusted under 35 U.S.C. 154(b) by 606 days.

(21) Appl. No.: 16/892,482

(22) Filed: Jun. 4, 2020

(65) Prior Publication Data
US 2021/0299414 A1  Sep. 30, 2021

(30) Foreign Application Priority Data
Mar. 31, 2020  (TR) ................................ 2020/05103

(51) Int. Cl.
*A61M 25/10* (2013.01)

(52) U.S. Cl.
CPC .... *A61M 25/1002* (2013.01); *A61M 25/1029* (2013.01); *A61M 2025/109* (2013.01); *A61M 2205/3331* (2013.01); *A61M 2210/105* (2013.01); *A61M 2210/1032* (2013.01); *A61M 2210/1042* (2013.01); *A61M 2210/1078* (2013.01); *A61M 2210/12* (2013.01)

(58) Field of Classification Search
None
See application file for complete search history.

(56) References Cited

U.S. PATENT DOCUMENTS

| 2008/0171985 A1* | 7/2008 | Karakoca | A61M 25/10 604/164.01 |
| 2015/0105729 A1* | 4/2015 | Valeti | A61M 25/0074 604/173 |

FOREIGN PATENT DOCUMENTS

EP  1913882 A1 * 4/2008 ..... A61B 17/320725

* cited by examiner

*Primary Examiner* — Dominic Lazaro
(74) *Attorney, Agent, or Firm* — Oppenhuizen Law PLC; David L. Oppenhuizen

(57) ABSTRACT

A catheter (1) resector balloon (8) used in the treatment of any type of endoluminal-endobronchial tumoral or non-tumoral narrowing and occlusions and endovascular obstructions seen in the hollow tubular organs such as the trachea, esophagus, urinary tract, biliary tract, etc. and vessels, characterized in that, it comprises the following; at least one flexible pad section with pressure and proximity sensor and/or pad section without pressure and proximity sensor which provides soft stopping at the final wall section where the catheter (1) resector balloon (8) is applied in a soft, flexible and shock absorber manner at the tip (2) portion, prevents punctures, tears, bursts or vascular damages occurred in the tissues and vessels formed as a region, undesired complications, provides stopping without giving any damage to its location.

12 Claims, 4 Drawing Sheets

RESECTOR BALLOON WITH SHOCK ABSORBER PADDING AND RIGID OR FLEXIBLE CATHETER

TECHNICAL FIELD OF THE INVENTION

The present invention relates to resector balloons used in the treatment of any type of endoluminal-endobronchial tumoral or non-tumoral constriction and obstructions and endovascular obstructions observed in the hollow tubular organs such as the trachea, esophagus, urinary tract, biliary tract, etc. and veins.

The present invention particularly relates to a resector balloon with shock absorber padding and rigid or flexible catheter which is formed as a section that enables soft stopping at the final wall section where it is applied as a soft, flexible, and shock-absorbing manner at the end of the resector balloon.

STATE OF THE ART

Resector balloons are used in the treatment of any type of endoluminal-endobronchial tumoral or non-tumoral constrictions and occlusions and endovascular obstructions observed in the hollow tubular organs such as the trachea, esophagus, urinary tract, biliary tract, etc. and vessels.

In the balloon application, which is one of the endobronchial treatment methods, the balloon is used as a buffer for the dilatation of the narrow bronchus and stopping hemorrhage in the region of bleeding. The balloon dilatation is implemented in order to expand the narrow bronchus, particularly the bronchial lumen before placing the stent based on the pressure of the tumor outside the bronchus. Moreover, the balloon tamponade is applied in order to control bleeding due to the tumor tissue in the trachea. Similar to the respiratory tract, balloon application is carried out in the expansion of the narrowing in the esophagus and the urinary tract and in controlling bleeding.

As a medical device, the resector balloons are used which are designed for opening the narrow areas in all endoluminal narrowing lesions and pathological events and to turn back the tubular organs and structures called lumens to their original openness. The operation principle of the rigid and flexible catheter resector balloon is based on the principle that undesired tissues are removed from their location with the effect of the damage occurred as a result of the compression and friction application of the braid or coating structure that covers the surface of the balloon as a result of the inflating and deflating processes of the balloon that are repeated in the narrowed regions.

The undesired tissues are cleaned from the narrowed luminal area or organ as a result of this effect. The area which performs the main shaving or scrapping process may be the area that covers the surface of the balloon, braid mesh, or an embossed surface which is obtained by any kind of spraying method. It is based on the principle of opening the narrowed lumens and providing the normal fluidity again as a result of inflating or deflating the medical device with any kind of balloon catheter which is covered with embossed surface or braid sheath or moving the same in a reciprocating manner or around itself.

The rigid or flexible catheter resector balloon device designed for opening the narrowed luminal structures is used to open the luminal narrowing in the organ and structures at a depth that cannot be visualized or cannot be followed by the imaging systems.

In case the resection process made at a depth that is not visible or cannot be visualized namely pushing the embossed balloon whose surface is coated or covered with a braided mesh into deep, damage may occur in the tissue.

The resections made in the deep parts of the tissue without seeing the same properly can lead to damage in tissues and vessels. The damage that occurred in the tissues and vessels may be in the form of puncture, tear, burst, or vessel damages. The vessel, bronchus, or other tissue damages can lead to non-recoverable cases and patient deaths.

In the patent application numbered TR 2006 05770, and titled flexible and rigid catheter resector balloon, the resector balloon structure disclosed is required to be developed and thus new technical developments are required regarding maintaining its functionality without damaging the tissue. While the resector balloon advances, the resections made without visualizing the deep parts of the tissues may lead to damages in the tissues and vessels. New technical developments are required in order to prevent this situation.

In the patent application numbered WO2014150813 belong to the year 2013, a hand-held resector balloon system comprises a balloon catheter that has a resection surface and a hub attached to a hand-held pump. The hub comprises an inflation hole which provides fluid to the first lumen of the catheter in order to inflate and deflate the balloon repeatedly for the resection of the biological material. However, the resections mentioned above which are made in the deep parts of the tissue without seeing the same properly can lead to damage in tissues and vessels. There are problems as not being able to carry out sufficient resections and causing damage in tissues and vessels with the resections made. In this regard, its structure is required to be developed.

It is required to study the new technical developments due to the problems described in the state of the art. New methods that facilitate the work of the surgeon and prevent the occurrence of life-threatening conditions due to vascular damage are required.

OBJECTS OF THE INVENTION

The object of the present invention, based on the state of the art, is to develop a resector balloon with shock absorber padding and rigid or flexible catheter, in which the disadvantages of the current structures are eliminated, that is formed as a section that enables soft stopping at the final wall section where it is applied, works in a soft, flexible and shock absorber manner at the catheter tip section following the resector balloon, prevents puncture, tear, burst or vascular damage in the tissues and vessels.

Another object of the invention is to provide a flexible structure to the tip portion of the catheter, thereby allowing the user to feel the contact in the tissue part on which this structure rests and applies force. When the pad at the tip portion of the catheter reaches the end of the organ or lumen or tubular area, the surgeon feels this and prevents harsh contact and prevents damage to the very thin vessel, bronchus, or other tissues.

Another object of the present invention is to prevent non-recoverable cases and patient deaths due to the vessel, bronchus, or other tissue damages in the areas where the resector balloon is applied.

Another object of the present invention is to facilitate the work of the surgeon and to provide a structure to the resector balloon that does not cause any damage to vessels, bronchus, or other tissues.

Another object of the present invention is to allow the surgeon to feel the last part of the tissue, vessels as the resector balloon advances and in this case not to damage tissues, vessels in the unseen area by the resector balloon.

In order to achieve these objects, a resector balloon with shock absorber padding and a rigid or flexible catheter is developed which prevents any potential damages to the lumen namely the walls of the vessel, bronchus or other tissues during its advance along the lumen since the pad region on the tip portion of the catheter is flexible and soft.

Figures 1, 2:
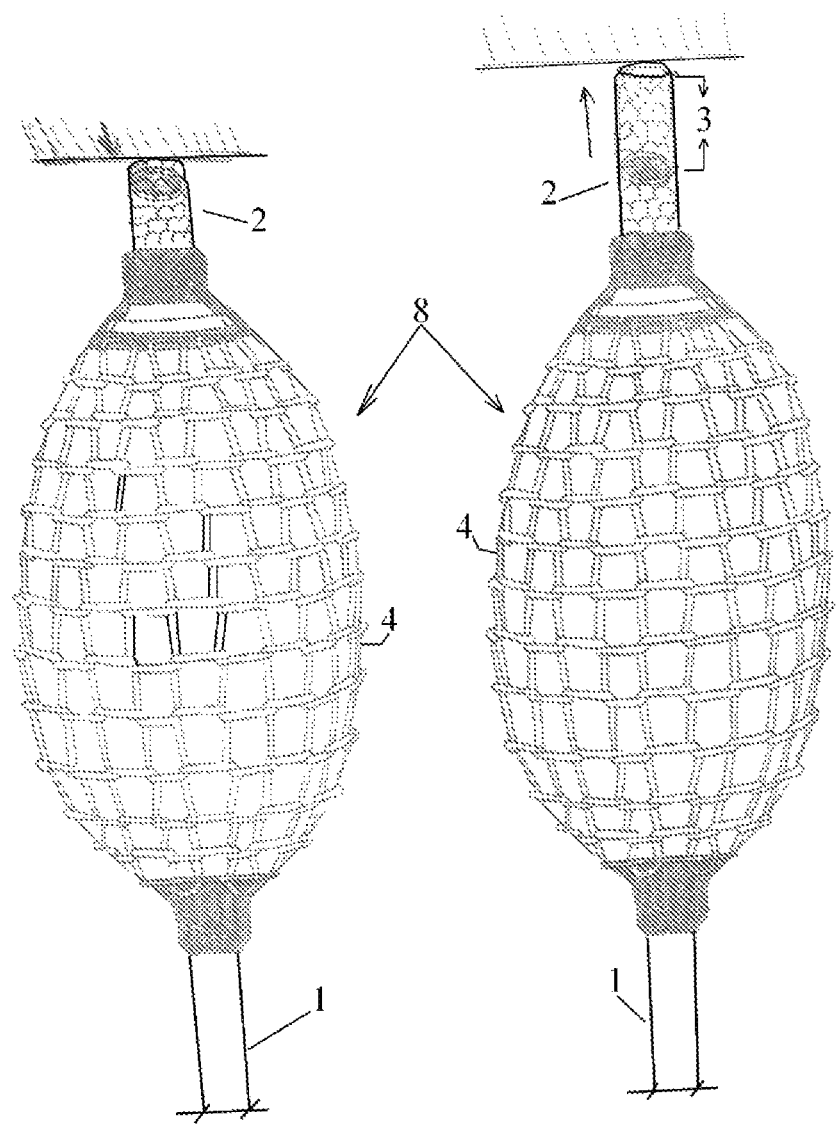
FIG. 1 illustrates the drawing of the flexible padded braided tip portion in a folded manner without damaging the tissue vessel part in an illustrative embodiment of the invention.
FIG. 2 illustrates the drawing of the flexible padded braided tip portion in an open, free manner in an illustrative embodiment of the invention.
Figures 3, 4:
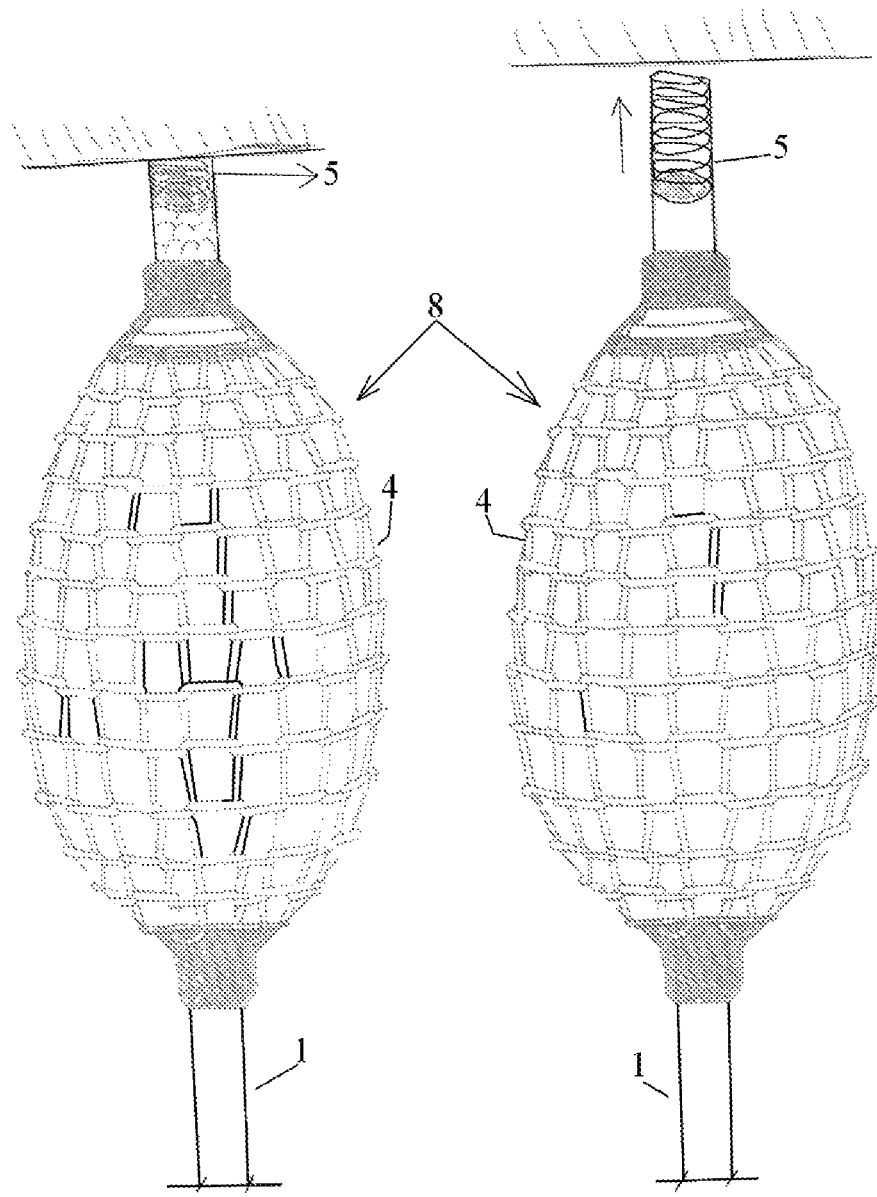
FIG. 3 illustrates the drawing of the flexible spring tip portion in a folded manner without damaging the tissue vessel part in an illustrative embodiment of the invention.
FIG. 4 illustrates the drawing of the flexible spring tip portion in an open, free manner in an illustrative embodiment of the invention.
Figures 5, 6:
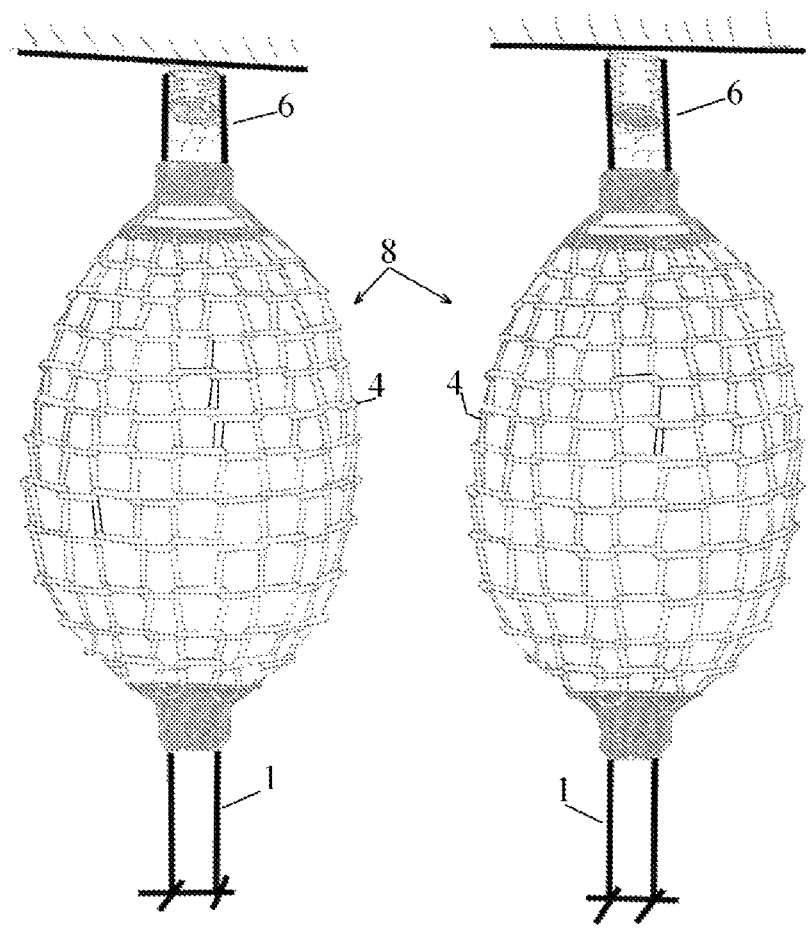
FIG. 5 illustrates the drawing of the flexible accordion tip portion in a folded manner without damaging the tissue vessel part in an illustrative embodiment of the invention.
FIG. 6 illustrates the drawing of the flexible accordion tip portion in an open, free manner in an illustrative embodiment of the invention.
Figures 7, 8:
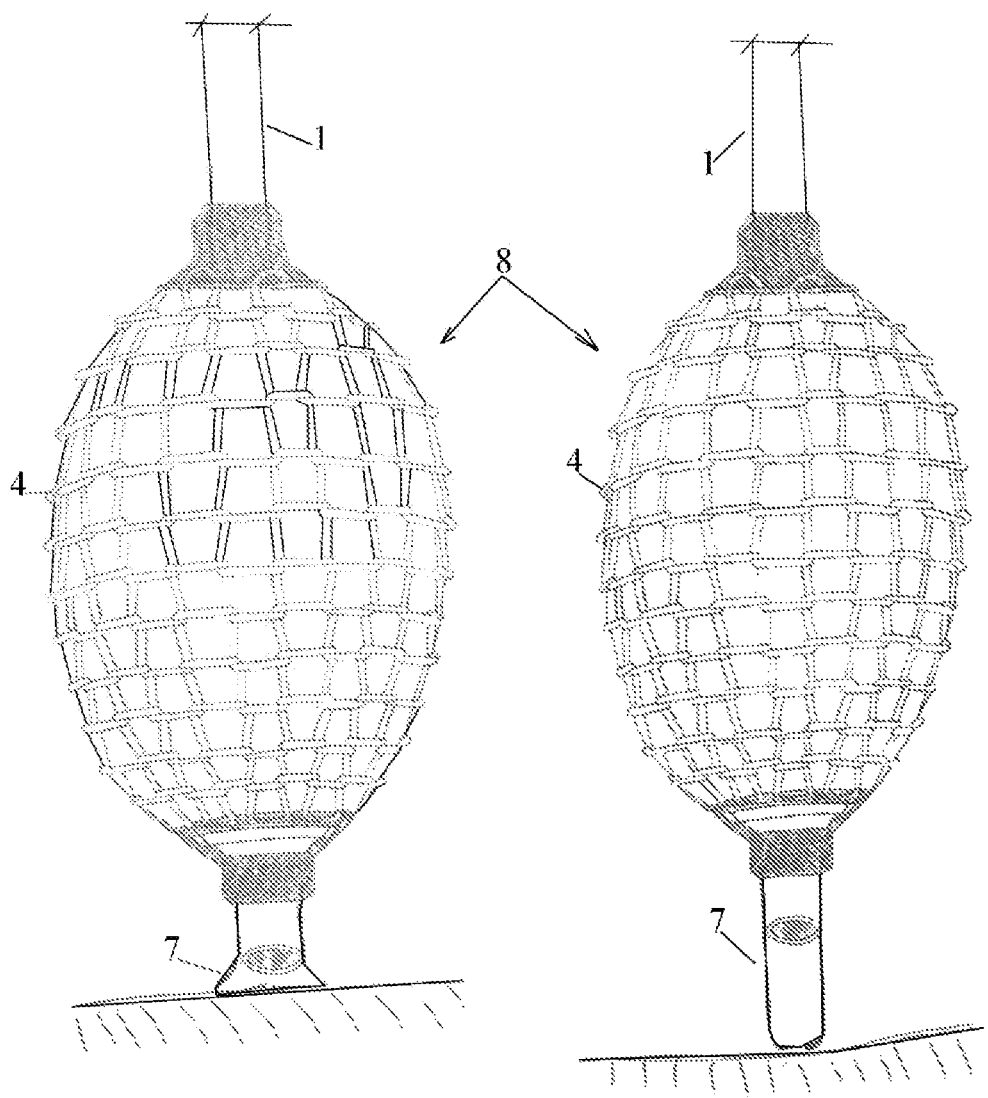
FIG. 7 illustrates the drawing of the flexible padded balloon tip portion in a folded manner without damaging the tissue vessel part in an illustrative embodiment of the invention.
FIG. 8 illustrates the drawing of the flexible padded balloon tip portion in an open, free manner in an illustrative embodiment of the invention.

| Reference Numerals | |
|---|---|
| 1 | Catheter |
| 2 | Tip |
| 3 | Flexible pad braid |
| 4 | Braid mesh sheath |
| 5 | Flexible spring tip |
| 6 | Flexible accordion tip |
| 7 | Flexible pad balloon tip |
| 8 | Balloon |

DETAILED DESCRIPTION OF THE INVENTION

An area that is soft, flexible, and shock-absorbing and enables soft stopping at the tip (2) portion of the shock absorber padded rigid or flexible catheter (1) resector balloon (8) that we newly developed is formed. The area which is present as a flexible area in the tip (2) portion of the catheter (1) slows down softly when the catheter (1) reaches to the last point of the organ and the tissue damage is prevented by means of the flexible pad braided (3) tip (2).

This area which is located on the tip (2) of the catheter (1) is flexible and it is intended for feeling the touch of the last part or resting point. The pad at the tip (2) portion of the catheter (1), flexible spring tip (5) or flexible accordion tip (6) or flexible pad balloon tip (7) region prevents harsh contact when it comes to the end of the organ or lumen or tubular area and prevents damage to the very thin vessel, bronchus or other tissues.

The pad region on the tip (2) portion of the catheter (1) is flexible and soft and prevents damage to the lumen namely the walls of the vessel, bronchus, or other tissues during its advance along the lumen. The padded rigid or flexible catheter (1) resector balloon (8) provides scraping and removing of any undesired structures that narrow the lumen without causing tissue damage at the thin and final points that it would reach by means of the flexible, soft pad texture at the tip (2) portion.

The padded rigid or flexible resector balloon (8) is covered with braided mesh sheath (4) structure which is obtained by a reverse braid with reverse knots. A braid mesh sheath (4) which is obtained as a braid which is reversely braided and is with external knots is formed in order to allow the padded rigid or flexible resector balloon (8) can function, namely make scrapping and shaving processes possible. Or a balloon (8) coated with a spraying method such that it becomes embossed is obtained. This area at the tip (2) portion of the padded rigid or flexible catheter (1) resector balloon (8) to which pad section is added can be a spring or a similar material.

The pad section may be obtained by means of bending like an accordion; the flexible accordion tip (6) may be manufactured from a plastic material. The pad section can be manufactured as a flexible, pad braid (3) from a material coated on the balloon (8). The pad section may be manufactured as an extension to the tip of the balloon of the scrapper material that is coated on the balloon (8). The pad section may be manufactured as a continuation of the tip (2) of the scrapping structure by means of extending the braid structure that coats the surface of the balloon (8) and reversing the same.

Moreover, a flexible pad section is obtained at the tip (2) of the balloon (8) catheter (1) by means of spraying or embossing or by extending the tip (2) portion of the balloon (8) a few mm from the rigid tip of the catheter (1).

This flexible pad portion will lead to a feeling of soft approach when the balloon (8) part catheter (1) is passed through the bronchoscope device and is pushed into deep areas of the bronchus and approaches to a narrow region or touches to the opposite tissue. Thus, this slow and soft approaching feeling is created with the effect of the balloon (8) which is extended or left long on the tip (2) portion of the catheter (1). The undesired complications such as damage, puncture, tear, and hemorrhage in luminal tissues are avoided by means of this flexible soft pad tip (2).

The invention relates to the catheter (1) resector balloons (8) used in the treatment of any type of endoluminal-endobronchial tumoral or non-tumoral narrowing and occlusions and endovascular obstructions seen in the hollow tubular organs such as the trachea, esophagus, urinary tract, biliary tract, etc. and vessels, characterized in that, it comprises the following; at least one flexible pad section with pressure and proximity sensor and/or pad section without pressure and proximity sensor which provides soft stopping at the final wall section where the catheter (1) resector balloon (8) is applied in a soft, flexible and shock absorber manner at the tip (2) portion, prevents puncture, tear, burst or vascular damages occurred in the tissues and vessels formed as a region, undesired complications, provides stopping without giving any damage to its location.

It comprises a tip (2) in the form of a pad section which serves as a flexible, pad in the continuation of the catheter (1), balloon (8) that allows feeling the touch in the tissue part that it rests or forces while it advances in the sections which cannot be seen by the surgeon during the operation.

The area which is present as a flexible area in the tip (2) portion of the catheter (1) comprises a flexible pad braided (3) tip (2) which enables the catheter (1) to slow down softly when the last point of the organ is reached and prevents tissue damage and enables to stop softly in a flexible and shock absorber manner.

The catheter (1), balloon (8) comprises pad, flexible spring tip (5) or flexible accordion tip (6) or flexible pad balloon tip (7) region on the tip (2) portion which prevents harsh contact when it comes to the end of the organ or lumen or tubular area and prevents damage to the very thin vessel, bronchus or other tissues.

The resector balloon (8) contains a reverse or plain braided mesh braid sheath (4) on it, the tip (2) contains a reverse or plain braided flexible pad braided (3) section on it.

The catheter (1) comprises at least one pressure and proximity sensor on the resector balloon (8) tip (2) that provides operation without giving damage by means of perceiving the pressure in its location.

The invention is a production method of a padded rigid or flexible catheter (1) resector balloon (8), characterized in that, it comprises the following process steps; forming at least one inflatable balloon (8) on the catheter (1), forming the region in the form of flexible pad section which enables stopping without damaging vessel, tissue at the last section following the balloon (8) by means of being stretched like a pad, creating a mesh braid sheath (4) or a hard surface on the balloon (8), making the catheter (1) balloon (8) connections.

A pad, flexible pad braided (3) tip (2) or flexible spring tip (5) or flexible accordion tip (6) or flexible pad balloon tip (7) region which provides stopping without giving damage to the tissue, vessel, at the tip (2) portion of the catheter (1), balloon (8) is formed.

At least one pressure, and proximity sensor is formed on the catheter (1) resector balloon (8) tip (2) which provides operation without giving damage by means of perceiving the pressure in its location.

I claim:

1. A padded catheter resector balloon for treating hollow tubular organs for endoluminal tumoral narrowing, endoluminal tumoral occlusions, endoluminal non-tumoral narrowing, endoluminal non-tumoral occlusions, endobronchial tumoral narrowing, endobronchial tumoral occlusions, endobronchial non-tumoral narrowing, endobronchial non-tumoral occlusions, and endovascular obstructions, characterized in that;
    the padded catheter resector balloon comprises at least one flexible, pad section which provides soft stopping at a final wall section of the hollow tubular organs, wherein the catheter resector balloon is applied in a soft, flexible and shock absorbing manner at a tip portion, thereby minimizing punctures, tears, bursts or vascular damage in the tissues and vessels of the hollow tubular organs.

2. The padded catheter resector balloon of claim 1, characterized in that;
    the tip portion is in the form of a pad section which serves as a flexible pad that allows feeling, contact and/or touch in a tissue part that the tip rests in, or forces through, while the padded catheter resector balloon advances in sections of the hollow tubular organs which cannot be seen by a surgeon during an operation.

3. The padded catheter resector balloon of claim 1, characterized in that;
    the tip portion of the padded catheter resector balloon comprises a flexible pad braided tip which enables the padded catheter resector balloon to slow down softly when a last point of the organ is reached, thereby minimizing tissue damage and enabling the padded catheter resector balloon to stop softly in a flexible and shock absorber manner.

4. The padded catheter resector balloon of claim 1, characterized in that;
    the tip portion of the padded catheter resector balloon comprises pad section, a flexible spring tip, flexible accordion tip, or flexible pad balloon tip region, which minimizes harsh contact when the tip portion comes to an end of an organ, lumen or tubular area, thereby minimizing damage to very thin vessels, bronchi or tissues.

5. The padded catheter resector balloon of claim 1, characterized in that;
    the tip portion of the padded catheter resector balloon comprises at least one pressure and proximity sensor, which provides operation without damaging the hollow tubular organs, wherein the at least one pressure and proximity sensor provides a means of perceiving pressure at a location of the tip portion during operation.

6. A catheter resector balloon used in treating hollow tubular organs for endoluminal tumoral narrowing, endoluminal tumoral occlusions, endoluminal non-tumoral narrowing, endoluminal non-tumoral occlusions, endobronchial tumoral narrowing, endobronchial tumoral occlusions, endobronchial non-tumoral narrowing, endobronchial non-tumoral occlusions, and endovascular obstructions, the catheter resector balloon comprising:
    a catheter and an expandable balloon, the catheter being secured to the expandable balloon at a first end thereof, the expandable balloon being covered by a braided mesh sheath; and
    a flexible tip secured to an end of the expandable balloon opposite to the first end thereof, the flexible tip configured to retract to a folded position or extend to an unfolded position, the flexible tip being a shock absorber to absorb force against the hollow tubular organs and to provide a user of the catheter resector balloon with resistance whereby the user is informed that the catheter resector balloon has been positioned against a final wall of the hollow tubular organ such that the catheter resector balloon does not damage the hollow tubular organ.

7. The catheter resector balloon of claim 6 wherein the catheter is rigid.

8. The catheter resector balloon of claim 6 wherein the catheter is flexible.

9. The catheter resector balloon of claim 6 wherein the flexible tip is formed from a plastic material.

10. The catheter resector balloon of claim 6 wherein the flexible tip includes a flexible spring.

11. The catheter resector balloon of claim 6 wherein the flexible tip includes a flexible accordion tip.

12. The catheter resector balloon of claim 6 wherein the flexible tip includes a flexible pad balloon tip.

* * * * *